United States Patent
Muller et al.

(10) Patent No.: US 6,291,216 B1
(45) Date of Patent: Sep. 18, 2001

(54) AFFINITY SUPPORTS CONTAINING LIGANDS BOUND TO OXIRANE GROUPS

(75) Inventors: Egbert Muller, Erzhausen; Kerstin Badel, Korschenbroich; Andreas Müller, Frankfurt am Main; Stephan Herbert, Sinnthal; Anna Seiler, Stockstadt (Main), all of (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 08/607,447

(22) Filed: Feb. 27, 1996

Related U.S. Application Data

(63) Continuation of application No. 08/162,185, filed as application No. PCT/EP93/00913 on Apr. 16, 1993, now abandoned.

(30) Foreign Application Priority Data

Apr. 16, 1992 (DE) .................................................. 42 12 730

(51) Int. Cl.[7] ............................ C12N 11/10; B01J 20/26; G01N 30/48; C07K 1/22
(52) U.S. Cl. .......................... 435/178; 435/177; 435/179; 435/180; 435/815; 502/401; 502/402; 530/413; 530/812; 530/813; 530/814; 530/815
(58) Field of Search .................................. 435/174, 177, 435/178, 179, 180, 181, 815; 530/402, 413, 810, 812, 813, 814, 815, 816; 502/401, 402

(56) References Cited

U.S. PATENT DOCUMENTS

| | | | |
|---|---|---|---|
| 3,844,892 | * 10/1974 | Matthews | 435/181 |
| 4,249,531 | * 2/1981 | Heller et al. | 424/426 |
| 4,332,694 | * 6/1982 | Kalal et al. | 252/189 |
| 4,352,884 | * 10/1982 | Nakashima et al. | 435/180 |
| 5,013,795 | * 5/1991 | Coleman et al. | 525/279 |
| 5,453,186 | * 9/1995 | Muller et al. | 210/198.2 |

FOREIGN PATENT DOCUMENTS

| | | | |
|---|---|---|---|
| 618332 | * 12/1991 | (AU) | . |
| 0165912 | * 12/1985 | (EP) | . |
| 0337144 | * 10/1989 | (EP) | . |
| 0292783 | * 10/1990 | (EP) | . |
| 0392735 | * 10/1990 | (EP) | . |
| 2476125 | * 8/1981 | (FR) | . |

OTHER PUBLICATIONS

Coleman, et. al., Journal of Chromatography, vol. 512, 1990, pp 345–363.*
Moreno, et. al., Applied Biochemistry and Biotechnology, vol. 31, 1991, pp. 43–51.*
Moreno, et. al., Journal of Molecular Catalysis, vol. 69, 1991, pp 419–427.*

* cited by examiner

Primary Examiner—David M. Naff
(74) Attorney, Agent, or Firm—Millen, White, Zelano & Branigan

(57) ABSTRACT

Activated support materials are provided containing oxirane or azlactone groups as substituents in linear polymers as activated groups. A base support containing hydroxyl groups is suspended in a solution containing cerium (IV) ions and a monomer containing an oxirane or azlactone group, and grafting polymerization is carrier out to produce a polymer containing oxirane or azlactone groups covalently bonded to the base support. Azlactone groups can be bonded to the base support via a thioether bond by using a base support containing thiol groups. The activated support materials can be used to prepare affinity supports containing an affinity ligand that is thiophilic or possesses a metal chelating group, or to prepare immobilized enzymes. The ligand can be iminodiacetic acid, or can be obtained by reacting an oxirane group of the support material with NaHS, and reacting the resultant product with divinylsulfone followed by reacting with mercaptoethanol.

12 Claims, No Drawings

AFFINITY SUPPORTS CONTAINING LIGANDS BOUND TO OXIRANE GROUPS

This application is a continuation of application Ser. No. 08/162,185, filed Dec. 16, 1993, now abandoned which is a 371 of PCT/EP93/00913 filed Apr. 16, 1993.

BACKGROUND OF THE INVENTION

The invention relates to activated support materials, and to affinity supports and immobilized enzymes which can be prepared from these activated support materials.

In affinity chromatography processes, specific interactions between the material to be analyzed and so-called affinity ligands are utilized to remove concomitant substances. The materials to be analyzed are bonded reversibly to the affinity ligands bonded to a support. Concomitant substances are not bonded and can therefore easily be washed out. The material to be analyzed is then liberated, utilizing the reversibility of the bonding. Liberation is effected, for example, by changes in pH, a change in ionic strength or by addition of dissolved affinity ligands to the eluting agent. Details of these processes and process variants are known to the expert.

The processes of affinity chromatography include purification of antibodies directed against a certain protein. The protein is bonded to a chromatographic support material. The solution which contains the antibodies to be purified is applied to the support material. The non-bonding portions of the antibody preparation are washed out and the purified antibodies are then eluted. In a reversal of this process, certain proteins can also be purified by means of affinity chromatography, an antibody directed against this protein being bonded to the chromatographic support material. In other applications of affinity chromatography, for example, coenzymes are bonded to the chromatographic support and serve to purify enzymes which bond this coenzyme. Instead of the coenzymes, dyestuffs can also be employed with similar success. A number of affinity ligands are summarized by way of example in Table 1. Other affinity ligands and materials to be analyzed as well as variants of processes are to be found in handbooks, for example in Kirk-Othmer Encyclopedia of Chemical Technology (page 35–40, 3rd edition, 1978, John Wiley and Sons) and in Protein Purification, Janson, J.-C. and Ryden, L. (editors) (page 275–325, 1989, VCH Publishers), or else in Vijayalakshimi, M. A. (1989; TIBTECH 7, page 71–76.

TABLE 1

| Affinity ligand | Material to be analyzed (Example) |
| --- | --- |
| Protein A | Immunoglobulins |
| Concanavalin A | Glycoproteins |
| Biotin | Avidin/streptavidin |
| Avidin | Biotin |
| Streptavidin | Biotin |
| 5'-adenosine monophosphate | AND-dependent oxidoreductases |
| 2',5'-adenosine diphosphate | NADP-dependent oxidoreductases |
| Aminoacridine | RNA or DNA |
| Boronic acid | Catecholamines |
| Boronic acid | Glycosylated hemoglobin |
| Iminodiacetic acid | Metalloproteins |
| "Thiophilic" ligands | Immunoglobulins |
| Cibachromium [sic] Blue | Monoclonal antibodies |

Different ligands are often required for affinity chromatography. It has therefore become established to provide activated support materials onto which the particular ligand can be bonded by simplified processes. One of the first products was BrCN-agarose: crosslinked agarose activated with cyanogen bromide. This reacts with primary amino groups of the ligand and thus bonds this to the support material. Improvements in respect of the stability of the support materials under pressure were obtained, for example, by introduction of crosslinked poly-(meth)acrylic acid derivatives or by the use of silica gel as the base material.

According to EP 064 833, silica gel is reacted with gamma-glycidoxypropyltrimethoxysilane, an activated support material being formed, onto the oxirane group of which affinity ligands can be bonded. According to DE 40 02 044, for example, "thiophilic" ligands are bonded to oxirane groups; these affinity supports are particularly suitable for the purification of immuno-globulins, for example of monoclonal antibodies. U.S. Pat. No. 4,737,560 describes activated support materials based on crosslinked polymers which comprise azlactone compounds as the active grouping. However, the bonding properties of these materials are unsatisfactory.

EP 0 172 579 describes support materials which have a core of silica gel, onto which a crosslinked polymer is applied. These polymers can contain the oxirane group, for example, as the activated group. The polymer is bonded to the support by reaction of some of the oxirane groups. This results in Si-O 9bonds, which are sensitive to hydrolysis. Since preshaped polymers are bonded to the silica gel, the charging density is limited. Crosslinking of the polymer moreover impedes access of high molecular compounds, such as proteins or nucleic acids.

Since the material to be analyzed in affinity chromatography is often a compound of high molecular weight ($>10^3$), the rate of mass transfer and therefore the productivity of the separation process is restricted by diffusion processes. U.S. Pat. No. 5,019,270 discloses chromatographic supports with which an accelerated mass transfer can be achieved, on the basis of a specific geometry of the support particles and the resulting liquid dynamics.

EP 0 295 073 discloses another method for accelerated mass transfer: the affinity ligands are rendered more accessible by using polyethylene glycol as a spacer. However, the bonding capacity of these materials is limited in a manner similar to that of materials according to EP 0 064 833.

Activated support materials such as are used for the preparation of affinity supports furthermore are in principle suitable for immobilizing enzymes. Such immobilized enzymes often have an improved stability. Moreover, they can easily be removed from the reaction batch and can also be re-used. Another use of immobilized enzymes is the provision of enzyme reactors with which a continuous reaction procedure is possible under flow-through conditions. However, it has been found that the the enzymes are often inactivated during the immobilization, and the yield of bonded enzyme after the bonding reaction is extremely low. In particular, the reactivity toward high molecular weight substrates (molecular weight $>10^3$) thereby drops. Benzonase, a nucleic acid hydrolase which hydrolyzes RNA and single- and double-stranded DNA into small, biologically inactive oligonucleotides, and proteinase K may be mentioned as examples of such enzymes which preferentially convert high molecular weight substrates and cannot be immobilized by methods known to date. Benzonase is capable of breaking down any nucleic acids still present in biologically obtained pharmaceutical active compounds, and thus of excluding undesirable transfer of genetic material. Such a process would preferably be carried out in a flow-through reactor. A precondition of this is immobilization of the benzonase on a suitable activated support while retaining the reactivity toward high molecular weight nucleic acids.

Other enzymes which present similar problems in their immobilization are known to the expert from the literature.

SUMMARY OF THE INVENTION

There is thus the object of providing an activated support material onto which affinity ligands or enzymes can be bonded in a simple manner. The resulting affinity supports should have a high bonding capacity and allow high mass transfer, and during immobilization of enzymes, the reactivity thereof, especially towards high molecular weight substrates, should be retained.

Surprisingly, it has been found that (meth)acrylic acid derivatives which contain an oxirane or an azlactone group, or the precursor of an azlactone group, can be grafted onto base supports which contain aliphatic hydroxyl groups on their surface. According to the invention, the polymerization is started here with cerium(IV) ions: G. Mino and S. Kaizerman (1958) J. Polymer Science 31, 242–243; G. Mino et al. (1959) J. Polymer Science 38, 393–401. The support materials obtainable by this method can be converted into affinity supports in a simple manner and have a high bonding capacity and a high mass transfer. Activated support materials with an azlactone grouping, the azlactone group of which is bonded to the support via a thioether bond, also show outstanding properties. These activated support materials also show particularly advantageous properties if the thioether bond is bonded directly to the base support.

DETAILED DESCRIPTION OF THE INVENTION

The invention thus relates to activated support materials based on base supports containing hydroxyl groups, on the surfaces of which polymers are covalently bonded, characterized in that a) the base support contains aliphatic hydroxyl groups, b) the covalently bonded polymers are bonded to the base support via a terminal monomer unit, c) the polymers contain monomer units of the formula I and d) the monomer units are linked linearly,

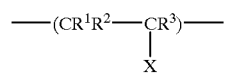

wherein $R^1$, $R^2$ and $R^3$ independently of one another are H or $CH_3$ and

X is an activated grouping containing an azlactone or an oxirane group.

The invention also relates to activated support materials which contain a radical corresponding to one of the formulae VIIa or VIIb

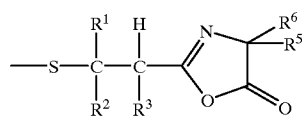

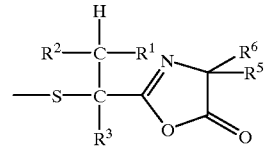

wherein $R^1$, $R^2$ and $R^3$ independently of one another are B or $CH_3$ and $R^5$ and $R^6$ in each case independently of one another are H or alkyl having 1–5 C atoms.

The invention relates to processes for the preparation of activated support materials starting from base supports containing hydroxyl groups, on the surfaces of which polymers are covalently bonded by grafting polymerization, characterized in that the base support particles containing hydroxyl groups are suspended and polymerized, in the presence of cerium (IV) ions, in a solution comprising monomers of the formula IV

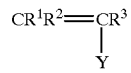

wherein $R^1$, $R^2$ and $R^3$ independently of one another are H or $CH_3$ and

Y is an activated or activatable grouping containing an oxirane or an azlactone group or a radical from which an azlactone group can originate, and, if appropriate, a precursor compound is converted into an azlactone ring system.

The invention also relates to processes for the preparation of activated support materials starting from base supports which contain thiol groups, by reaction with a vinylazlactone of the formula VIII

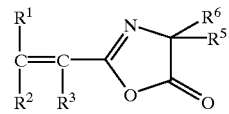

wherein $R^1$, $R^2$ and $R^3$ independently of one another are H or $CH_3$ and $R^5$ and $R^6$ in each case independently of one another are H or alkyl having 1–5 carbon atoms.

The invention relates to the use of the activated support materials according to the invention for bonding affinity ligands and for immobilizing enzymes.

The invention also relates to processes for the preparation of affinity supports, characterized in that affinity ligands, which are known in detail to the expert, are bonded to activated support materials according to the present invention.

The invention also relates to affinity supports which can be prepared by bonding affinity ligands to the activated support materials according to the invention.

The invention furthermore relates to the use of affinity supports according to the present invention in the purification of biopolymers.

The invention also relates to processes for the immobilization of enzymes, characterized in that enzymes are bonded to activated support materials according to the present invention.

The invention also relates to immobilized enzymes which can be prepared by immobilization of enzymes on the activated support materials according to the invention, and the use thereof for enzymatic reactions.

The structure of the support materials according to the invention results from the reaction sequence originally described by Mino et al.: the primary or secondary hydroxyl groups of the base support material are converted into carbon or possibly also oxygen radicals by reaction with cerium(IV) salts in strongly acid aqueous solution. A free radical chain reaction starts on these radicals, the monomers added being incorporated into the chain. This chain is linear and is linked to the aliphatic radical of the base support with a monomer unit. The polymerization is ended radical termination reactions with participation of the cerium(IV) salts. The (average) chain length can therefore be influenced by the concentration ratios of the base support, the initiator and the monomers. Uniform monomers or else mixtures of different monomers can be employed; in the latter case, grafted copolymers are formed.

The following reaction sequence is used for the preparation of the activated support materials with an azlactone grouping, the azlactone group of which is bonded to the support via a thioether bond:

a) If the base support has neither thiol nor oxirane radicals, oxirane radicals are first introduced. For this, either aliphatic hydroxyl groups of the base support are reacted with epichlorohydrin, or (meth)acrylic glycidyl esters are grafted onto aliphatic hydroxyl groups of the base support. Thiol groups are then introduced by reaction of the oxirane radicals with sodium bisulfide in an alkaline medium by known processes.

b) The thiol groups of the base support introduced in the first step or already present beforehand are then added onto the vinyl double bond of a vinylazlactone derivative. This reaction is preferably catalyzed by 1,8-diazabicyclo[5,4,0]-undec-7-ene in accordance with EP 0 473 457. Vinyldimethylazlactone is the particularly preferred vinylazlactone derivative.

Base supports in the context of the present invention are particles onto which polymers are grafted. Generally customary porous or non porous support particles can be employed as the base supports as long as they contain primary or secondary aliphatic hydroxyl groups on their surface. Suitable materials are, inter alia, polysaccharides based on agarose, cellulose, cellulose derivatives and polymers based on dextran. Polymers based on polyvinyl alcohol or copolymers of (meth)acrylate derivatives and comonomers with aliphatic hydroxyl groups are preferred. Diol-modified silica gels are particularly preferred base supports. Preferred commercially obtainable base supports are Fractogel® TSK HW 65 (S) (E. Merck), a porous vinyl-based copolymer which contains aliphatic hydroxyl groups (1 milliequivalent of OH/g), and LiChrospher® DIOL (B. Merck), a diol-substituted silica gel, likewise with aliphatic hydroxyl groups.

Base supports in the wider sense, however, are also membrane- or thread-like and net-like or woven-like materials which contain aliphatic hydroxyl groups or into which aliphatic hydroxyl groups can be introduced by processes which are known per se. These materials can also contain additional support elements for improving their mechanical stability. These materials can likewise be converted into activated support materials by using their aliphatic hydroxyl groups. The same reaction sequences as are described below for particulate base supports are essentially used here.

Affinity ligands are chemical compounds which are capable of undergoing specific interactions and which are therefore suitable for use in affinity chromatography. Examples of such affinity ligands are summarized in Table 1.

Activated groups in the sense of the invention are chemically reactive radicals which are present covalently bonded to the monomers or the monomer units of polymers and which undergo covalent bonding with the affinity ligand. Activated groups in the sense of the invention are, in particular, radicals according to formula II, which contain an oxirane group, and radicals according to formula III, which contain an azlactone group.

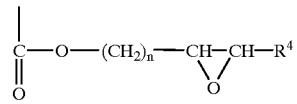

II

In formula II $R^4$ is H, alkyl having 1–5 C atoms or aryl having 6–12 C atoms and n is an integer between 1 and 5.

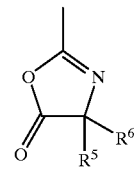

III

In formula III $R^5$ and $R^6$ independently of one another are H or alkyl having 1–5 C atoms.

Activated support materials are base supports on which polymers with activated groups are present in bonded form. Affinity supports are base supports onto which polymers with affinity ligands are bonded, bonding thereof being effected with the aid of the activated groups.

Enzymes are proteins which act as biocatalysts. However, nucleic acid derivatives which have catalytic functions (so-called ribozymes) and are likewise subsumed according to the invention under the term "enzymes" are also known. Enzymes catalyze certain reactions specifically, for example redox reactions or hydrolyses, in which certain substrates, for example alcohols or nucleic acids, are reacted. Cofactors are often required by the enzymes in these reactions. In metabolism, several enzymes often act together to catalyze reaction chains. Details of enzymatically catalyzed reactions, the enzymes and cofactors which participate in these, and of biochemical reaction chains are known to the expert. It is furthermore known that enzymes can be immobilized on support materials by means of various reactants, for example oxirane, carbonylimidazole or tresyl derivatives. If various enzymes act together in a reaction chain, these can also be immobilized in close proximity on a support in order to keep the diffusion paths for intermediate products short. According to the invention, enzymes can therefore be immobilized individually, or various enzymes, for example which cooperate in reaction chains, can also be immobilized together.

Activatable groups in the context of the present invention are radicals which contain precursor compounds for activated groups; carboxylate derivatives according to formula VI, which can be converted into azlactone groups according to formula III, may be mentioned as an example.

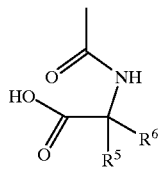

VI

In formula VI $R^5$ and $R^6$ independently of one another are H or alkyl having 1–5 C atoms.

$R^1$ and $R^2$ in the formulae I, IV and V preferably are H; that is to say acrylic and methacrylic acid derivatives are preferred.

In formula II, n is preferably 1, 2 or 3 and $R^4$ preferably is H, methyl, ethyl or propyl. The (2,3-epoxypropyl) radical is particularly preferred as the compound of the formula II; that is to say n=1 and $R^4$=H.

In the formulae III, VI, VIIa, VIIb and VIII, the radicals $R^5$ and $R^6$ are preferably the same, that is to say optically inactive compounds are preferred. The radicals $R^5$ and $R^6$ preferably are H, methyl, ethyl or propyl. The two radicals particularly preferably are either H or methyl; that is to say the derivatives of glycine and of 2-methylalanine, as well as the associated azlactones are particularly preferred.

The vinyl groups of the vinylazlactone derivatives used are preferably not substituted, that is to say $R^1$, $R^2$ and $R^3$ in the formulae VIIa, VIIb and VIII preferably are H.

In exceptional cases, it may be beneficial to limit the possible charging density of the support materials. For this, in addition to the monomers according to formula I, monomers according to formula V which contain no activated groups are preferably additionally employed.

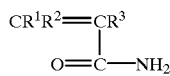

V

In formula V, $R^1$, $R^2$ and $R^3$ have the same meanings as in formula I. 60–99.5% of monomers according to formula IV and 0.5–40% of monomers according to formula V are preferably employed in the preparation of the copolymers.

Where they are not commercially obtainable, the monomers according to the formulae IV and V are accessible by standard processes known to the expert: examples of such standard processes are Schotten-Baumann acylation and Strecker synthesis. Details of these processes are described in the usual handbooks, for example Houben-Weyl, Methoden der Organischen Chemie [Methods of Organic Chemistry], Georg Thieme Verlag, Stuttgart.

Grafting polymerization by the Mino and Kaizerman method is carried out in purely aqueous, nitric acid solution by known processes. This reaction can therefore be carried out only with readily water-soluble monomers. However, it has been found, surprisingly, that reaction with cerium(IV) salts is also possible if a mixture of water and organic solvents which contain no hydroxyl groups is used as the solvent. Dioxane or tetrahydrofuran are particularly preferred here. The content of organic solvent in the reaction batch is preferably 10–80% by volume, particularly preferably 20–50% by volume.

Since it is known that oxirane groups can be hydrolyzed by treatment with dilute mineral acids, it is surprising that monomers which contain oxirane groups can be polymerized by means of cerium(IV) salts in mineral acid solution and the oxirane structure is retained.

The precursor compounds for azlactone groups according to formula VI which are contained in the graft polymers are converted into azlactone groups by processes known to the expert. Reaction with acetic anhydride is preferred for this purpose.

After preparation of the affinity supports, activated groupings which have not reacted in general still remain. These groups are usually converted by reaction with an excess of a water-soluble amino or thiol compound. Aminoethanol is preferably used for this purpose. If the affinity ligand is stable to hydrolysis, the excess activated groupings can also be removed hydrolytically by means of dilute oxygen-containing mineral acids, such as, for example, sulfuric or nitric acid. Reaction (duration: 1–5 hours) with 0.5 M sulfuric acid at 35–60° C. is preferred here.

It has been found that affinity supports which have a higher bonding capacity than customary support materials can be prepared from the activated support materials according to the invention. The mass transfer and therefore the productivity of the affinity supports is also improved. These advantages are evidently based on the provision of a large number of activated groups on the activated support material, these groups being bonded by flexible linear polymers. During preparation of affinity supports, the activated groups, which are particularly favorable sterically, react. These affinity supports furthermore are more resistant to the action of acids or bases than conventional support materials which are not coated with polymer. Immobilized enzymes which can be prepared from the activated support materials according to the invention also have improved properties when these are compared with enzyme preparations which have been immobilized on conventional support materials.

Even without further embodiments, it is assumed that an expert can utilize the above description in the broadest scope. The preferred embodiments are therefore to be interpreted merely as a descriptive disclosure and in no way as a limiting disclosure in any manner.

The complete disclosure of all the Applications, Patents and Publications mentioned above and below and of the corresponding Application DE 42 12 730, filed on Apr. 16, 1992, are introduced into this Application by reference.

EXAMPLES

The following examples serve to illustrate the invention and are not a limitation of the invention.

In the following Preparation Examples, room temperature (RT) is 15–30° C. The polymerization is carried out in a three-necked flask of suitable size fitted with a stirrer, dropping funnel and thermometer. Washing is carried out by filtration with suction on a suction filter.

Example 1

Preparation of an Oxirane-activated Support Starting from Fractogel®-TSK HW 65 (S)

2 g of ammonium cerium(IV) nitrate (dissolved in 25 ml of 2 M $HNO_3$) are mixed with a suspension of 50 ml of sedimented Fractogel®-TSK HW 65 (S) and 25 ml of water at RT, while stirring vigorously. After 1 minute, a solution of 3 g of 2,3-epoxypropyl methacrylate in 30 ml of dioxane is added. Stirring is continued for 3 hours. The reaction suspension is then washed first with distilled water and then with 0.05 M EDTA solution.

Example 2

Preparation of an Oxirane-activated Support Starting from LiChrospher®-Diol

The preparation is carried out in accordance with Example 1, LiChrospher®-DIOL (particle size 15–25 μm. pore size 80 nm) being used as the base support instead of Fractogel®-TSK HW 65 (S).

Example 3

Preparation of an Affinity Support for Metal Chelate Chromatography Based on Fractogel®

200 ml of a 0.4 M solution of the disodium salt of iminodiacetic acid are added to 100 ml of suction-filtered oxirane-activated support material prepared according to Example 1 (pH=11). The solution is stirred at 45° C. for 24 hours. The reaction product is filtered off with suction and washed with water and the unreacted oxirane groups are hydrolyzed by treatment with 200 ml of 0.5 M sulfuric acid (2 hours, 45° C.).

The affinity support material is then washed with 0.2 M sulfite solution (pH=2), and with 1 M nitric acid and 0.5 M sodium hydroxide solution.

Example 4

Preparation of an Affinity Support for Metal Chelate Chromatography Based on LiChrospher®-Diol 200 ml of a 0.4 M solution of the disodium salt of iminodiacetic acid are added to 100 ml of suction-filtered oxirane-activated support material prepared according to Example 2 (pH=9). The solution is stirred at 45° C. for 24 hours. The reaction product is filtered off with suction and the unreacted oxirane groups are hydrolyzed by treatment with 200 ml of 0.5 M sulfuric acid (2 hours, 45° C.).

The affinity support material is then washed with 0.2 M sulfite solution (pH=2) and with 1 M nitric acid. Finally, it is washed neutral with Na phosphate buffer (0.1 H; pH 7).

Example 5

Preparation of an Affinity Support for "Thiophilic" Protein Adsorption Based on Fractogel®-TSK HW 65 (S)

Stage 1:
100 ml of suction-filtered oxirane-activated support material prepared according to Example 1 are suspended in 200 ml of 4 M NaHS solution (pH=11) and the suspension is stirred at room temperature for 1 hour. It is then washed with distilled water.

Stage 2:
200 ml of a 0.4 M divinylsulfone solution (dissolved in a 0.5 M Na₂CO₃ solution; pH=11) are added to the material obtained in Stage 1 and the mixture is stirred at room temperature for one hour. The gel is then washed with distilled water.

Stage 3:

The material obtained from Stage 2 is stirred in 200 ml of 2.3 M mercaptoethanol in 0.5 M Na$_2$CO$_3$ solution (pH=11) for 45 minutes. The product is then washed in each case twice with in each case 200 ml of 0.2 M sulfite solution (pH=1), 1 M nitric acid and 0.05 M NaOH. The resultant affinity ligand is of the formula

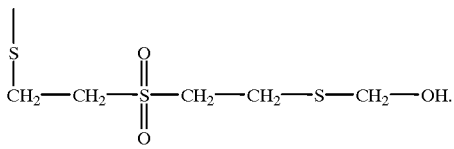

Example 6

Preparation of an Affinity Support for "thiophilic" Protein Adsorption Based on LiChrospher®-DIOL Stage 1:
100 ml of suction-filtered oxirane-activated support material prepared according to Example 2 are suspended in 200 ml of 4 M NaHS solution (pH=9) and the suspension is stirred at room temperature for 1 hour. It is then washed with distilled water.

Stage 2:
200 ml of a 0.4 M divinylsulfone solution (dissolved in a 0.5 M Na$_2$CO$_3$ solution; pH=9) are added to the material obtained in Stage 1 and the mixture is stirred at room temperature for one hour. The gel is then washed with distilled water.

Stage 3:
The material obtained from Stage 2 is stirred in 200 ml of 2.3 M mercaptoethanol in 0.5 M Na$_2$CO$_3$ solution (pH=9) for 45 minutes.

The product is then washed in each case twice with in each case 0.2 M sulfite solution (pH=1) and 1 M nitric acid. Finally, it is washed neutral with Na phosphate buffer (0.1 M; pH 7).

Example 7

Preparation of an Azlactone-activated Support Starting from Fractogel®-TSK HW 65 (S)

Stage 1: Graft Polymer Comprising poly-(acryloylmethylalanine)

For the reaction, the starting substance is suspended and a monomer solution and an initiator solution are prepared. Monomer solution: 5 g of acryloyl-2-methylalanine are dissolved in 20 ml of water with addition of 4 M NaOH. After addition of 50 ml of dioxane, the mixture is heated to 45° C. The pH is then brought to pH=1.5 with 25% HCL [sic].

Initiator solution: 3.5 g of ammoniumcerium(IV) nitrate are dissolved in 50 ml of 2 M HNO$_3$.

Suspension of the starting material: 75 ml of sedimented gel Fractogel® TSK HW 65 (S) are suspended in 75 ml of distilled water and the suspension is diluted with 100 ml of dioxane, while stirring vigorously (about 200 revolutions per minute).

The suspension of the starting material is heated to 45° C., and the apparatus is evacuated and flushed with argon.

The initiator solution is added, the mixture is left 1 minute, and the monomer solution, heated to 45° C., is then added. The batch is stirred at 45° C. for 3 hours. After cooling to room temperature, the product is washed with 0.2 M sulfite solution (pH=1), 0.5 M NaOH and acetone. The gel is then dried at 60° C. for 24 hours.

Stage 2: Cyclization to the Azlactone Derivative 500 ml of acetic anhydride are added to the product obtained in Stage 1 and the mixture is stirred at 100° C. for 2 hours. The product is filtered off with suction and dried at 60° C. in a vacuum drying cabinet for 24 hours.

Example 8

Preparation of an Azlactone-activated Support Starting from LiChrospher®-DIOL

Stage 1: Graft Polymer Comprising poly-(acryloylmethylalanine)

For the reaction, the starting substance is suspended and a monomer solution and an initiator solution are prepared.
Monomer solution: 5 g of acryloyl-2-methylalanine are dissolved in 20 ml of water with addition of 4 M NaOH. After addition of 50 ml of dioxane, the mixture is heated to 45° C. The pH is then brought to pH=1.5 with 25% HCL [sic].
Initiator solution: 3.5 g of ammonium cerium(IV) nitrate are dissolved in 50 ml of 2 M $HNO_3$.
Suspension of the starting material: 75 ml of sedimented gel LiChrospher®-DIOL are suspended in 75 ml of distilled water and the suspension is diluted with 100 ml of dioxane, while stirring vigorously (about 200 revolutions per minute).

The suspension of the starting material is heated to 45° C., and the apparatus is evacuated and flushed with argon.

The initiator solution is added, the mixture is left 1 minute, and the monomer solution, heated to 45° C., is then added. The batch is stirred at 45° C. for 3 hours. After cooling to room temperature, the product is washed with 0.2 M sulfite solution (pH=1), and Na phosphate buffer (0.1M; ph 7). The gel is then dried at 60° C. for 24 hours.

Stage 2: Cyclization to the Azlactone Derivative 500 ml of acetic anhydride are added to the product obtained in Stage 1 and the mixture is stirred at 100° C. for 2 hours. The product is filtered off with suction and dried at 60° C. in a vacuum drying cabinet for 24 hours.

Example 9

Preparation of an Affinity Support Which Contains Protein A 20 mg of protein A are dissolved in a mixture of 10 ml of 1 M ammonium sulfate solution and 25 ml of Na phosphate buffer (20 mM; pH=7.5). 1 g of azlactone-activated support material from Example 7 is added and the suspension is shaken at room temperature for 24 hours.

50 ml of aqueous ethanolamine solution (1 M) are then added to the suspension and the mixture is shaken for a further hour. Thereafter, the product is filtered off with suction and washed with 25 mM Na phosphate+0.15 M NaCl (pH=7.5).

The affinity support obtained in this way bonds 20 mg of gamma-globulin per gram of moist gel (in 50 mM TRIS buffer, pH 8, with 9 g/l of NaCl).

Example 10

Preparation of an Azlactone-activated Support, the Azlactone Radicals of Which are Bonded Via Thioether Bridges Stage 1: Introduction of the Epoxide Groups 250 ml of Fractogel® HW 65 (S) (E. Merck, DE) are suspended in a solution of 15 g of NaOH in 100 ml of water. 60 ml of epichlorohydrin are added dropwise in the course of 20 minutes, while stirring. The temperature is then increased to 70° C. and the mixture is stirred for 90 minutes. The suspension is then allowed to cool to room temperature again, and the gel is filtered off with suction. The gel is then washed with in each case 200 ml: 3×water, 2×methanol and 2×water.

Stage 2: Introduction of the Thiol Groups

The product from Stage 1 is suspended in 1000 ml of 0.5 M sodium carbonate buffer pH 11, 200 g of NaHS (monohydrate, Art. No. 17.150 78 (Jansen Chimica, DE) are added, while stirring, and the mixture is stirred for one hour. The product is then filtered off with suction, washed 3× with 200 ml of water and resuspended in 500 ml of 0.5 M sulfuric acid. The suspension is heated to 60° C., while stirring, and stirred for two hours. The product is filtered off with suction and washed 5× with in each case 200 ml of water and 3× with in each case 200 ml of acetone and then dried (60° C.; 16 hours).

Stage 3: Addition of the Thiol Groups to vinyldimethylazlactone 7 g of vinyldimethylazlactone are dissolved in 35 ml of dimethylformamide, and 3.5 g of thiol-derivatized Fractogel® from Stage 2 are suspended in the solution. 600 μl of 1,8-diazabicyclo(5.4.0)undec-7-ene (Art. No. 803282; B. Merck/DE) are added and the mixture is stirred at room temperature for 24 hours. The gel is filtered off with suction, washed 3× with in each case 50 ml of dioxane and extracted with 300 ml of ethyl acetate in a Soxhlett [sic] apparatus for 16 hours. The gel is filtered off with suction again, washed 3× with in each case 50 ml of dioxane and 3× with in each case 50 ml of acetone and dried at 60° C. for 16 hours.

Example 11

Preparation of an Azlactone-activated Support, the Azlactone Radicals of Which are Bonded by Thioether Bridges Solutions:

a) Starter Solution:

4 g of ammonium cerium(IV) nitrate and 7.5 g of nitric acid (content: 65%) are dissolved in 500 ml of water.

b) Monomer Solution:

3.8 g of 2,3-epoxypropyl methacrylate are dissolved in 100 ml of 1,4-dioxane.

Stage 1: Grafting Polymerization 250 ml of sedimented Fractogel® TSK HW65 (S) are suspended in 125 ml of water. The starter solution is added, while stirring, and the mixture is stirred for one minute. The monomer solution is then added, while stirring. After stirring for 3 hours, the gel is filtered off with suction over a glass filter suction filter and treated with in each case 250 ml of the following washing solutions: 2×water, 1×0.05 M sodium phosphate buffer (pH 7), 1×water, 1×0.05 M EDTA solution, 2×water, 2×acetone and 2×diethylether. The product is dried at 35° C. in a vacuum drying cabinet. Elemental analysis gave: C: 53.7%; H: 7.6%; N: 0.4%.

Stage 2: Introduction of the Thiol Groups

The product from Stage 1 is suspended in 1000 ml of 0.5 M sodium carbonate buffer pH 11, 200 g of NaHS (monohydrate, Art. No. 17.150 78 (Jansen Chimica, DE) are added, while stirring, and the mixture is stirred for one hour. The product is then filtered off with suction, washed 3× with 200 ml of water and resuspended in 500 ml of 0.5 M sulfuric acid. The suspension is heated to 60° C., while stirring, and stirred for two hours. The product is filtered off with suction and washed 5× with in each case 200 ml of water and 3× with in each case 200 ml of acetone and then dried (60° C.; 16 hours).

Stage 3: Addition of the Thiol Groups to vinyldimethylazlactone 7 g of vinyldimethylazlactone are dissolved in 35 ml of dimethylformamide, and 3.5 g of thiol-derivatized Fractogel® from Stage 2 are suspended in the solution. 600 µl of 1,8-diazabicyclo(5.4.0)undec-7-ene (Art. No. 803282; E. Merck/DE) are added and the mixture is stirred at room temperature for 24 hours. The gel is filtered off with suction, washed 3× with in each case 50 ml of dioxane and extracted with 300 ml of ethyl acetate in a Soxhlett [sic] apparatus for 16 hours. The gel is filtered off with suction again, washed 3× with in each case 50 ml of dioxane and 3× with in each case 50 ml of acetone and dried at 60° C. for 16 hours.

Example 12

Immobilization of Protein A on an Azlactone-activated Support, the Azlactone Radicals of Which are Bonded Via Thioether Bridges 50 mg of protein A are dissolved in 10 ml of buffer A (25 mM sodium phosphate; pH 7.5; 1 M sodium sulfate) and 2 g of aclactone-derivatized [sic] Fractogel® from Example 10 are suspended in this solution. The suspension is shaken on a shaking machine for 24 hours. The gel is then filtered off with suction and washed 3× with in each case 20 ml of buffer B (25 mM sodium phosphate; pH 9.0; 1 M ethanolamine) and suspended in 50 ml of buffer B and shaken again for 5 minutes. The gel is filtered off with suction again, washed 3× with in each case 20 ml of buffer C (50 mM Tris; pH 7.4; 9 g/l of NaCl) and suspended in 50 ml of buffer C.

Example 13

Immobilization of Benzonase on an Epoxy-activated Support

Solutions:
 a) Starter Solution:
  3 g of ammonium cerium(IV) nitrate and 3 g of nitric acid (content: 65%) are dissolved in 190 ml of water.
 b) Monomer Solution:
  6 g of 2,3-epoxypropyl methacrylate are dissolved in 44 ml of 1,4-dioxane.
 c) Buffer I:
  25 mM Tris/HCl, 0.5 mM $MgCl_2$, pH 8.0; 50% by volume of ethylene glycol
 d) Buffer L:
  25 mM Tris, 2.5 mM $CaCl_2$, pH 7.5; 50% by volume of ethylene glycol Stage 1: Grafting of a Linear Polymer Containing Epoxide Groups onto Fractogel® TSK HW65 (S)

100 ml of sedimented Fractogel® TSK HW65 (S) are suspended in 66 ml of water. The starter solution is added, while stirring, and the mixture is stirred for one minute. The monomer solution is then added, while stirring. After stirring at 180 revolutions per minute at room temperature for 1 hour, the gel is filtered off with suction over a glass filter suction filter and treated with in each case 150 ml of the following washing solutions: 4×water, 3×acetone, 3×water, 1×10% sulfuric acid, 2×water, 1×0.2 M phosphate buffer (pH 7), 3×water, 3×acetone, 1×diethylether. The activated gel is dried at 35° C. in a vacuum drying cabinet.

Stage 2: Reaction of the Benzonase with the Activated Gel

800 µl of benzonase solution (1800 kU/ml) are dissolved in 20 ml of buffer I. 2.5 g of the activated gel from Stage 1 are suspended in this solution. The reaction mixture is shaken in a conical flask (200 revolutions per minute) at room temperature for 20 hours. The gel is filtered off with suction over a glass filter suction filter and treated with in each case 20 ml of the washing solution listed below: 2× with buffer I, 1× with water, 2× with buffer L. The gel is filtered off with suction, washed 3× with 20 ml of fresh sterile buffer L and then stored in buffer L at 4° C.

Example 14

Immobilization of Proteinase K on an Epoxy-activated Support

Solutions:
 a) Starter Solution:
  15 g of ammonium cerium(IV) nitrate and 15 g of nitric acid (content: 65%) are dissolved in 950 ml of water.
 b) Monomer Solution:
  30 g of 2,3-epoxypropyl methacrylate are dissolved in 220 ml of 1,4-dioxane.
 c) Buffer I:
  25 mM barbiturate, 5 MM $MgCl_2$, pH 9.2
 d) Buffer I [sic]:
  50 mM Tris, 5 mM $CaCl_2$, pH 7.5

Stage 1: Grafting of a Linear Polymer Containing Epoxide Groups onto Fractogel® TSK HW65 (S)

500 ml of sedimented Fractogel® TSK HW65 (S) are suspended in 330 ml of water. The starter solution is added, while stirring, and the mixture is stirred for one minute. The monomer solution is then added, while stirring. After stirring at 180 revolutions per minute at room temperature for 1 hour, the gel is filtered off with suction over a glass suction filter and treated with in each case 500 ml of the following washing solutions: 4×water, 3×acetone, 3×water, 1×10% sulfuric acid, 2×water, 2×0.2 M phosphate buffer (pH 7), 3×water.

Stage 2: Reaction of Proteinase K with the Activated Gel 25 g of proteinase K (catalogue No. 24568; E. Merck, DE) are dissolved in 5000 ml of buffer I. The activated gel from Stage 1 is suspended in this solution. The reaction mixture is stirred in a three-necked flask at room temperature for 22 hours. After 18 hours, the pH is adjusted to 9.2 with sodium hydroxide solution. The gel is filtered off with suction over a glass filter suction filter and treated with in each case 500 ml of the washing solutions listed below: 2× with buffer I, 1× with 5 mM $CaCl_2$ in water, 2× with an aqueous solution containing 1 M NaCl and 5 mM $CaCl_2$, 1× with 5 mM $CaCl_2$ in water, 2× with an aqueous solution containing 0.1 M sodium acetate (pH 4) and 5 mM $CaCl_2$, 1× with 5 mM $CaCl_2$ in water, 2× with aqueous 6 M urea solution, 3× with 5 mM $CaCl_2$ in water, 2× with buffer L. The gel is filtered off with suction, washed 3× with 500 ml of fresh sterile buffer L and then stored in buffer L at 4° C.

It can be seen from the above examples that the activated support materials according to the invention are outstandingly suitable for the preparation of affinity supports, and that the affinity supports prepared therefrom have improved properties for affinity chromatography. It can furthermore be seen that the activated support materials according to the invention are outstandingly suitable for immobilization of enzymes, the activity thereof, in particular towards high molecular weight substrates, being largely retained.

USE EXAMPLES

Use Example A

Protein-bonding Capacity of Various Metal Chelate Affinity Supports

Chromatographic conditions:

| | |
|---|---|
| Apparatus: | Merck-Hitachi HPLC inert system |
| Column: | Superformance ® 50-10 mm (E. MERCK) |
| Flow rate: | 1 ml/minute |
| Eluent: | 20 mM Na phosphate buffer (pH = 7) and 1 M NaCl |
| Sample: | 10 mg/ml of lysozyme, dissolved in the eluent |
| Wavelength: | 280 nm |

The results are summarized in Table 2.

TABLE 2

Protein-bonding capacity of various metal chelate affinity supports

| | Bonding in mg of lysozyme/ml of gel | |
|---|---|---|
| | conventional | according to the invention |
| Comparison material[1] | 40 | — |
| Base support: | | |
| Fractogel ® TSK BW 65 (S) | 36[2] | 65 |
| Lichrospher ® [sic]]DIOL | 35[3] | 70 |

Explanations:
[1] Commercially obtainable affinity support
[2] Activation of the base support in accordance with the prior art by means of epichlorohydrin
[3] Activation of the base support in accordance with the prior art by means of gamma-glycidoxypropyltrimethoxysilane

Use Example B

Protein-bonding Capacity of Various "Thiophilic" Affinity Supports

Chromatographic conditions:

| | |
|---|---|
| Apparatus: | Merck-Hitachi HPLC inert system |
| Column: | Superformance ® 50-10 mm (E. MERCK) |
| Flow rate: | 0.25 ml/minute |
| Eluent: | 20 mM Na phosphate buffer (pH = 7) and 0.8 M ammonium sulfate |
| Sample: | 5 mg/ml of gamma-globulin, dissolved in the eluent |
| Wavelength: | 280 nm |

The results are summarized in Table 3.

TABLE 3

Protein-bonding capacity of various "thiophilic" affinity supports

| | Bonding in mg of gamma-globulin/ml of gel | |
|---|---|---|
| | conventional | according to the invention |
| Comparison material[1] | 35 | — |
| Comparison material[2] | 42 | — |
| Base support: | | |
| Lichrospher ® [sic] DIOL | 30[2] | 52 |

Explanations:
[1] Commercially obtainable affinity support based on agarose
[2] Activation of the base support in accordance with the prior art by means of gamma-glycidoxypropyltrimethoxysilane

Use Example C

Separation of Human Serum Albumin (HSA) and Human IgG (immunoglobulin G) on a Protein A-containing Affinity Support Chromatographic conditions:

| | |
|---|---|
| Apparatus: | Merck-Hitachi HPLC inert system |
| Column: | Superformance ® 25-10 mm (E. MERCK) |
| Sorbent: | Affinity support based on Fractogel ® TSK HW 65 (S) (prepared according to Example 9) |
| Flow rate: | 1 ml/minute |
| Eluent A: | 50 mM TRIS (pH 7.4) + NaCl (9 g/l) |
| Eluent B: | 1 M acetic acid |
| Step gradient: | After 10 minutes, change to eluent B |
| Sample: | 2 mg of HSA and 1 ml of human IgG in 200 μl of eluent A |
| Wavelength: | 280 nm |

Results

Human serum albumin elutes in the solvent front after 2 minutes, while human IgG is eluted only by eluent B after 14 minutes.

Use Example D

Chromatographic Separation of Human IgG (immunoglobulin G) from Human Serum on Various Protein A-containing Affinity Supports The bonding properties of two products with immobilized protein A were compared:

a) Protein A bonded without thioether groups (support: Sepharose): sorbent A b) Protein A bonded according to Example 12 (sorbent B)

In each case 250 p1 of gel, equilibrated with buffer A (25 mM Tris/HCl; pH 8.0) are introduced into a mini-column (500 μl; Mobitec/DE). A mixture of 250 μl of human serum and 250 μl of buffer A are [sic] applied and the column is washed with 2 ml of buffer A. It is then eluted with 2 ml of buffer B (50 mM glycine/HCl; pH 3.0). The amount of immunoglobulin G (IgG) in the serum sample and in the eluate are determined by means of an immunoturbidimetric test. The results are summarized in Table 4.

TABLE 4

|         | Serum | Sorbent A | Sorbent B |
|---------|-------|-----------|-----------|
| IgG (mg) | 3.15 | 1.05 | 2.67 |
| %       | 100  | 33   | 84   |

Use Example E

Determination of the Activity of Immobilized Benzonase

DNA preparations with various molecular weights (Hind: Hind III fragment of LAMBDA-DNA, pBr: plasmid pBr 322, LAMBDA: DNA of the phage LAMBDA) are incubated (shaken at 37° C.) with immobilized benzonase prepared according to Example 13 and the content of high molecular weight substrate in the reaction supernatant is determined at various times (1, 4, 16 minutes) by electrophoresis on agarose gel (0.8%). The immobilized benzonase is suspended in Tris buffer pH 8.0 (50 mM Tris, 1 mM $MgCl_2$, 50% by volume of glycerol, 0.5% by volume of mercaptoethanol); in each case 10 μl of suspension are employed. 50 μl of the particular DNA solution are added to the benzonase suspension and the mixture is incubated.

|  | Time: | | |
|---|---|---|---|
| Substrate: | 1 | 4 | 16 |
| Hind[1)] | -- | -- | -- |
| pBr[2)] | -- | -- | -- |
| LAMBDA[3)] | ++ | + | − |

Explanation:
++ High molecular weight contents essentially present
+ High molecular weight contents significantly broken down
− High molecular weight contents essentially broken down
-- High molecular weight contents no longer detectable
[1)]Fragments with a length of 23,130, 9416, 6557, 4361, 2322, 2027, 564 and 125 base pairs
[2)]4361 base pairs
[3)]48,502 base pairs stirred for hours. The reaction product is filtered off with suction and washed with water and the unreacted oxirane groups are hydrolyzed by treatment with 200 ml of 0.5 M sulfuric acid (2 hours, 45° C.).

What is claimed is:

1. An affinity support material, comprising an affinity ligand bound to a base support material, wherein said affinity support material comprises:
   (a) a base support material containing aliphatic hydroxyl groups,
   (b) a polymer bonded to said aliphatic hydroxyl groups of said base support material via a terminal monomer unit of said polymer, wherein more than one monomer unit of said polymer is linked linearly to said terminal monomer unit and each of the said monomer units are of the formula I:

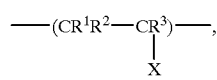

and, wherein $R^1$, $R^2$, and $R^3$, independently of one another, are H or $CH_3$, and X is an activated grouping containing an oxirane group, and
   (d) an affinity ligand is bonded through X to said base support material and said affinity ligand is thiophilic or possesses a metal chelation group.

2. An affinity support material according to claim 1, wherein said affinity ligand is of the formula:

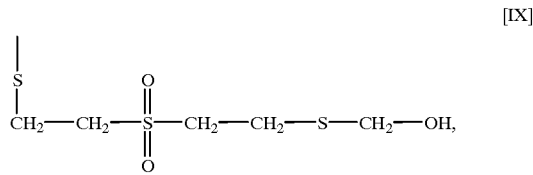

wherein:
$R^1$, $R^2$, and $R^3$, independently on one another are, H or $CH_3$;
$R^4$ is H, alkyl having 1–5 C atoms, or aryl having 6–12 C atoms.

3. An affinity support material according to claim 1, wherein said affinity ligand is a thiophilic group.

4. An affinity support material according to claim 1, wherein said base support is an agarose polysaccharide, a cellulose, or a dextran polymer.

5. An affinity support material according to claim 1, wherein said base support is a polyvinyl alcohol polymer or a (meth)acrylate copolymer.

6. An affinity support material according to claim 1, wherein said base support is a diol-modified silica gel.

7. An affinity support material according to claim 1, wherein said activated grouping containing an oxirane group is a radical according to formula II

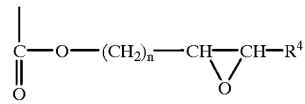

wherein
$R^4$ is H, alkyl having 1–5 C atoms, or aryl having 6–12 C atoms, and n is an integer of 1–5.

8. An affinity support material according to claim 7, wherein n is 1, 2 or 3 and $R^4$ is H, methyl, ethyl or propyl.

9. An affinity support material according to claim 8, wherein n is 1 and $R^4$ is H.

10. An affinity support material according to claim 1, wherein said polymer is a copolymer which contains, in addition to monomer units in accordance with formula I, monomer units obtained from monomers of formula V:

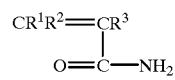

wherein $R^1$, $R^2$, and $R^3$, independently of one another are H or $CH_3$.

11. An infinity support material according to claim 1, wherein said affinity ligand is iminodiacetic acid.

12. An affinity support material according to claim 1, wherein said affinity ligand is obtained by reacting the oxirane group with NaHS, reacting the resultant product with divinylsulfone, followed by reaction with mercaptoethanol.

* * * * *

UNITED STATES PATENT AND TRADEMARK OFFICE
CERTIFICATE OF CORRECTION

PATENT NO. : 6,291,216 B1 Page 1 of 1
APPLICATION NO. : 08/607447
DATED : September 18, 2001
INVENTOR(S) : Muller et al.

It is certified that error appears in the above-identified patent and that said Letters Patent is hereby corrected as shown below:

on Title page
item (75) Inventors: line 3, reads "Frankfurt am Main;" should read -- Frankfurt; --
    line 4, reads "Anna" should read -- Anja --
Column 17, line 65, delete "(d)" and insert -- (c) --
Column 18, line 4, delete "[IX]"
Column 18, line 14, reads "independently on" should read -- independently of --
Column 18, line 14, reads "another are," should read -- another, are --

Signed and Sealed this

Fifteenth Day of August, 2006

JON W. DUDAS
*Director of the United States Patent and Trademark Office*